(12) United States Patent
Ahmadi et al.

(10) Patent No.: US 10,195,007 B2
(45) Date of Patent: Feb. 5, 2019

(54) DETERMINING THE INTERNAL STRUCTURE OF A BONE

(71) Applicants: Mohsen Ahmadi, Tehran (IR); Arash Khojasteh, Tehran (IR); Mohammad Esmaeelinejad, Tehran (IR); Seyed Farzad Aghdashi, Tehran (IR)

(72) Inventors: Mohsen Ahmadi, Tehran (IR); Arash Khojasteh, Tehran (IR); Mohammad Esmaeelinejad, Tehran (IR); Seyed Farzad Aghdashi, Tehran (IR)

(*) Notice: Subject to any disclaimer, the term of this patent is extended or adjusted under 35 U.S.C. 154(b) by 0 days.

(21) Appl. No.: 15/475,033

(22) Filed: Mar. 30, 2017

(65) Prior Publication Data

US 2017/0202637 A1 Jul. 20, 2017

Related U.S. Application Data

(60) Provisional application No. 62/315,030, filed on Mar. 30, 2016.

(51) Int. Cl.
| *A61C 1/00* | (2006.01) |
| *A61C 19/04* | (2006.01) |
| *A61B 5/00* | (2006.01) |
| *A61C 1/05* | (2006.01) |
| *A61C 1/08* | (2006.01) |

(52) U.S. Cl.
CPC ............ *A61C 19/04* (2013.01); *A61B 5/4509* (2013.01); *A61B 5/4547* (2013.01); *A61B 5/746* (2013.01); *A61C 1/055* (2013.01); *A61B 2562/0247* (2013.01); *A61C 1/084* (2013.01)

(58) Field of Classification Search
CPC ........... A61C 19/04; A61C 1/055; A61C 1/08; A61B 5/4509
See application file for complete search history.

(56) References Cited

U.S. PATENT DOCUMENTS

| 4,961,674 A | 10/1990 | Wang |
| 6,665,948 B1 | 12/2003 | Kozin et al. |
| 8,402,829 B2 | 3/2013 | Halevy-Politch et al. |
| 9,033,707 B2 | 5/2015 | Dricot |
| 2006/0084034 A1* | 4/2006 | Hochman ............ A61C 8/0033 433/173 |
| 2007/0287933 A1* | 12/2007 | Phan .................. A61B 10/0233 600/566 |
| 2009/0220563 A1* | 9/2009 | Shachar ................ A61C 8/00 424/423 |

(Continued)

*Primary Examiner* — Nicholas Lucchesi
(74) *Attorney, Agent, or Firm* — NovoTechIP International PLLC

(57) ABSTRACT

A drill burr includes a channel, extending along a longitudinal axis of the drill burr, and fluidically connected to a water reservoir for providing a constant-flow liquid jet. The constant-flow liquid jet has a first pressure directed at the bone along the longitudinal axis of the drill burr. A pressure sensor senses a pressure change in the liquid jet from the first pressure to a second pressure. A signal processing unit is configured to translate the pressure change into information indicating a structural change in the bone along the drilling path, from a first structure to a second structure, corresponding respectively to the first pressure and the second pressure. Optionally, the signal processing unit generates an audio alarm notifying of the structural changes.

19 Claims, 7 Drawing Sheets

(56) References Cited

U.S. PATENT DOCUMENTS

| | | | |
|---|---|---|---|
| 2010/0081111 A1* | 4/2010 | Better | A61C 8/0018 |
| | | | 433/174 |
| 2010/0081112 A1* | 4/2010 | Better | A61C 8/0018 |
| | | | 433/174 |
| 2010/0221681 A1 | 9/2010 | Hochman | |
| 2011/0287386 A1* | 11/2011 | Better | A61C 8/0018 |
| | | | 433/174 |
| 2012/0237893 A1* | 9/2012 | Bergheim | A61C 5/02 |
| | | | 433/81 |
| 2012/0310247 A1* | 12/2012 | Hsieh | A61B 17/1626 |
| | | | 606/80 |
| 2013/0040267 A1* | 2/2013 | Bergheim | A61C 3/03 |
| | | | 433/216 |

\* cited by examiner

DETERMINING THE INTERNAL STRUCTURE OF A BONE

CROSS REFERENCE TO RELATED APPLICATION

This application claims the benefit of priority from U.S. Provisional Patent Application Ser. No. 62/315,030, filed on Mar. 30, 2016, and entitled "A DRILLING DEPTH DETERMINER FOR DENTAL IMPLANTS," which is incorporated herein by reference in its entirety.

TECHNICAL FIELD

The present disclosure generally relates to a method and device for determining internal structures of a bone during surgery, particularly to a method and device for determining internal structures of a bone during implant surgery, and more specifically relates to a method and device for determining internal structures of a bone using changes in a liquid jet flow pressure.

BACKGROUND

Natural teeth may be lost as a result of dental diseases or trauma making it desirable for replacement with a dental implant. A dental implant may be surgically positioned within the mandibular or maxillary alveolar bone. A screw hole may be drilled in the mandibular or maxillary alveolar bone for fixing the dental implant in the bone.

When drilling through the mandibular or maxillary alveolar bone, the oral surgeon has to decide on a drilling axis for the implant, while being aware to avoid contact between the drill burr and the adjacent soft tissue. Generally, the decision may be made based on the surgeon's knowledge of the jawbone structure into which the implant is to be inserted, the position of the nerve tissues within the jawbone structure, and the surface area of the gum on which the dental implant must be placed. Different techniques, such as X-ray imaging, computer tomography (CT) and panoramic imaging may be utilized to assess the jawbone structure, the position of the nerve tissues, and the surface area of the gum.

The imaging methods mentioned above are generally considered for pre-surgical assessment of implant sites and do not provide the surgeon with required information in real time during surgery.

Therefore, there is a need in the art for methods and devices for interactive determination of a proximity of the drill burr to a region of change in bone structure, or a change from bone structure to adjacent soft tissue.

SUMMARY

In one general aspect, the present disclosure describes a system for determining an internal structure of a bone along a drilling path. In an implementation, the system may include a drill, and a hollow drill burr, supported by and rotatable by the drill, extending along a longitudinal axis to a distal end, and including a channel along the longitudinal axis, the channel including an outlet at the distal end. In an implementation, the drill can be configured to receive a liquid from a liquid reservoir, at a first pressure, and pass the fluid through the channel while rotating the hollow drill burr, and the hollow drill can be configured to direct the fluid, while drilling a bone, as a liquid jet from directed at the bone. In an implementation, the system can include a pressure sensor configured to sense a pressure change in the liquid jet from the first pressure to a second pressure, and can include a signal processing unit configured to process said pressure change into information related to the structural changes in the bone along the drilling path from a first structure to a second structure.

In one general aspect, the present disclosure describes a method for determining an internal structure of a bone along a drilling path. In an implementation, one exemplary method can include drilling a bone with a hollow drill burr having a distal end and a channel including an outlet at the distal end and, while drilling the bone, receiving at the hollow drill burr a liquid at a first pressure, and passing the fluid through the channel to exit from the outlet as a liquid jet directed at the bone; sensing a pressure in the liquid jet; detecting, based on the sensing, a pressure change in the liquid jet from the first pressure to a second pressure; and upon detecting the pressure change, generating a user-detectable information indicative of the pressure change.

BRIEF DESCRIPTION OF THE DRAWINGS

While the specification concludes with claims particularly pointing out and distinctly claiming the subject matter that is regarded as forming the present application, it is believed that the application will be better understood from the following description taken in conjunction with the accompanying DRAWINGS, where like reference numerals designate like structural and other elements, in which:

DETAILED DESCRIPTION

Figure 1:
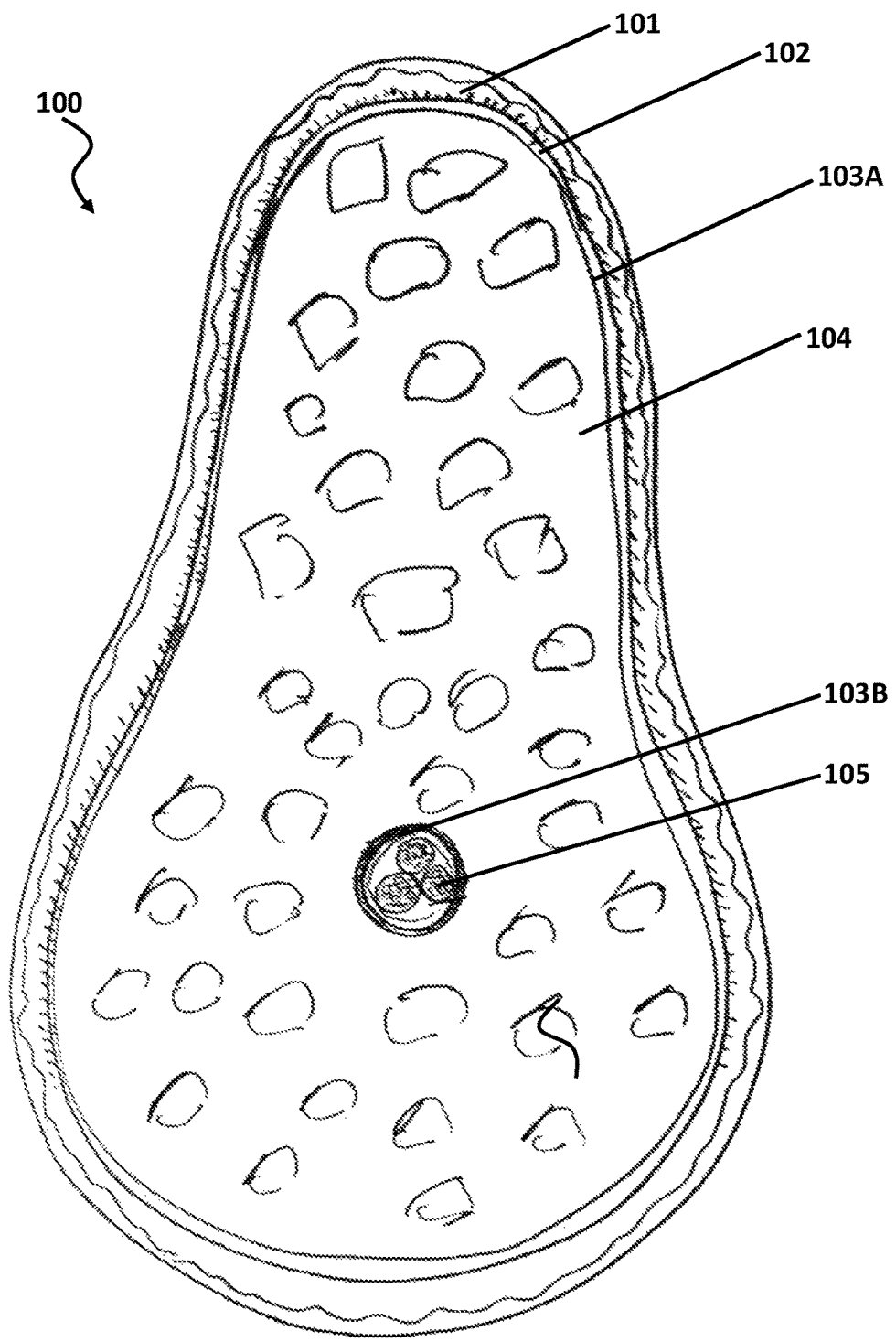
FIG. 1 shows a cross sectional view of a mandible.

In a dental implant surgery, the oral surgeon may drill a hole in the mandible to screw the implant in the bone. FIG. 1 shows a cross sectional view of a mandible as known in the art. Referring to FIG. 1 a mandible 100 may include oral mucosa 101, periosteum 102, cortical bones 103A-B, cancellous bone 104, and neurovascular bundle 105. When drilling through the mandible 100, the oral surgeon has to decide on a drill axis for the implant, while being aware to avoid contact between the drill burr and the neurovascular bundle 105.

Disclosed herein is a method and device that can provide a user information to help the surgeon to avoid contact between the drill burr and the neurovascular bundle 105 by determining the internal structure of the mandible 100 along a drilling path.

In an implementation of the present disclosure, a liquid jet may be applied on the drilling surface with an internal structure while the liquid jet pressure is measured simultaneously. The internal structure may have a plurality of layers with different material resistances. The liquid jet may first be applied on a first internal structure with a first material resistance. When the drill burr passes from the first internal structure to a second internal structure with a second material resistance, the liquid jet pressure may change.

The changes in liquid jet pressure may be sensed using a pressure sensor. The sensed pressures may then be transformed into signals by the sensor, and the signals may be sent to a signal processing unit. The signal processing unit may be configured, for example by computer executable instructions stored in a memory coupled to a digital processor, transform the signals to user-interpretable results. The user-interpretable results may be presented in visual form, for example on an LCD display, or in audio form via a buzzer, or both. This apparatus therefore provides the user, for example an oral surgeon, information on reaching a point or boundary of changes in the internal structure of the bone. The user can then adjust or maintain a drilling or other operation within a desired position relative to the change boundary in bone structure. For example, in use by an oral surgeon, the visual or audible information can assist the surgeon in avoiding contact between the drill burr and the neurovascular bundle 105.

Systems and methods according to this disclosure are not limited to dental surgery and, instead, can be adapted to and applied and a wide range of surgeries involving the use of a medical tool, intended to penetrate into a tissue or bone for creating a perforation or cavity in the tissue or bone structure in contact with a membrane. Such surgeries can be in the field of the orthopedics, or general surgery.

According to one or more exemplary embodiments, the present disclosure may be incorporated in a drill. However, the present disclosure is not limited to such incorporation, and a basic system, in accordance with some preferred embodiments of the present invention, may include only a probe to determine the internal structural changes.

Figure 2:
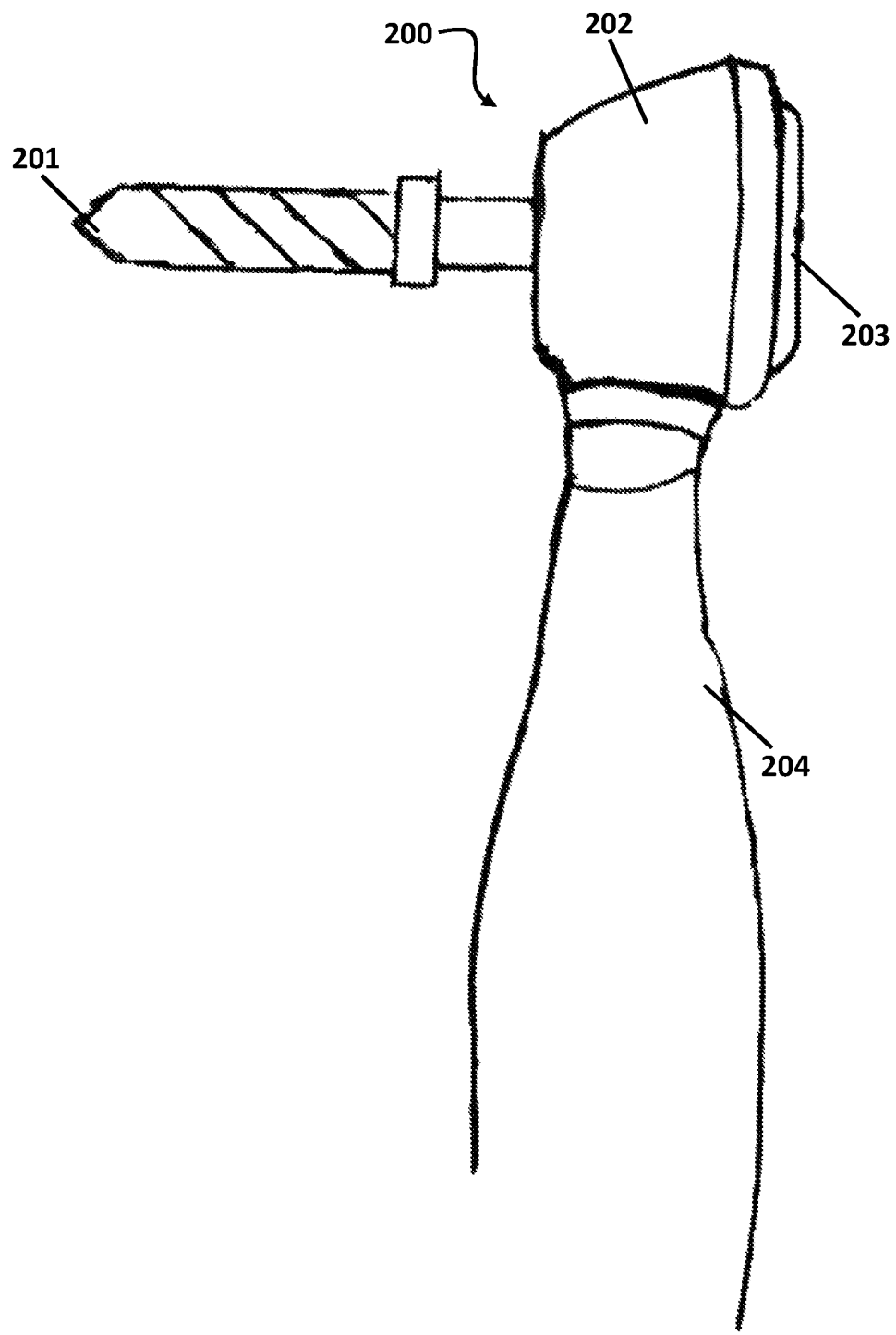
FIG. 2 shows an exemplary dental drill.

FIG. 2 shows an exemplary dental drill 200 as known in the art. The dental drill 200 may include a drill burr 201, a head 202, an end cap 203, and a body 204. Water or air may be supplied through the body 204, to rotate a turbine placed in the head 202 of the drill 200. The turbine may convert the air or water pressure to mechanical energy to rotate the drill burr 201.

Figure 3A:
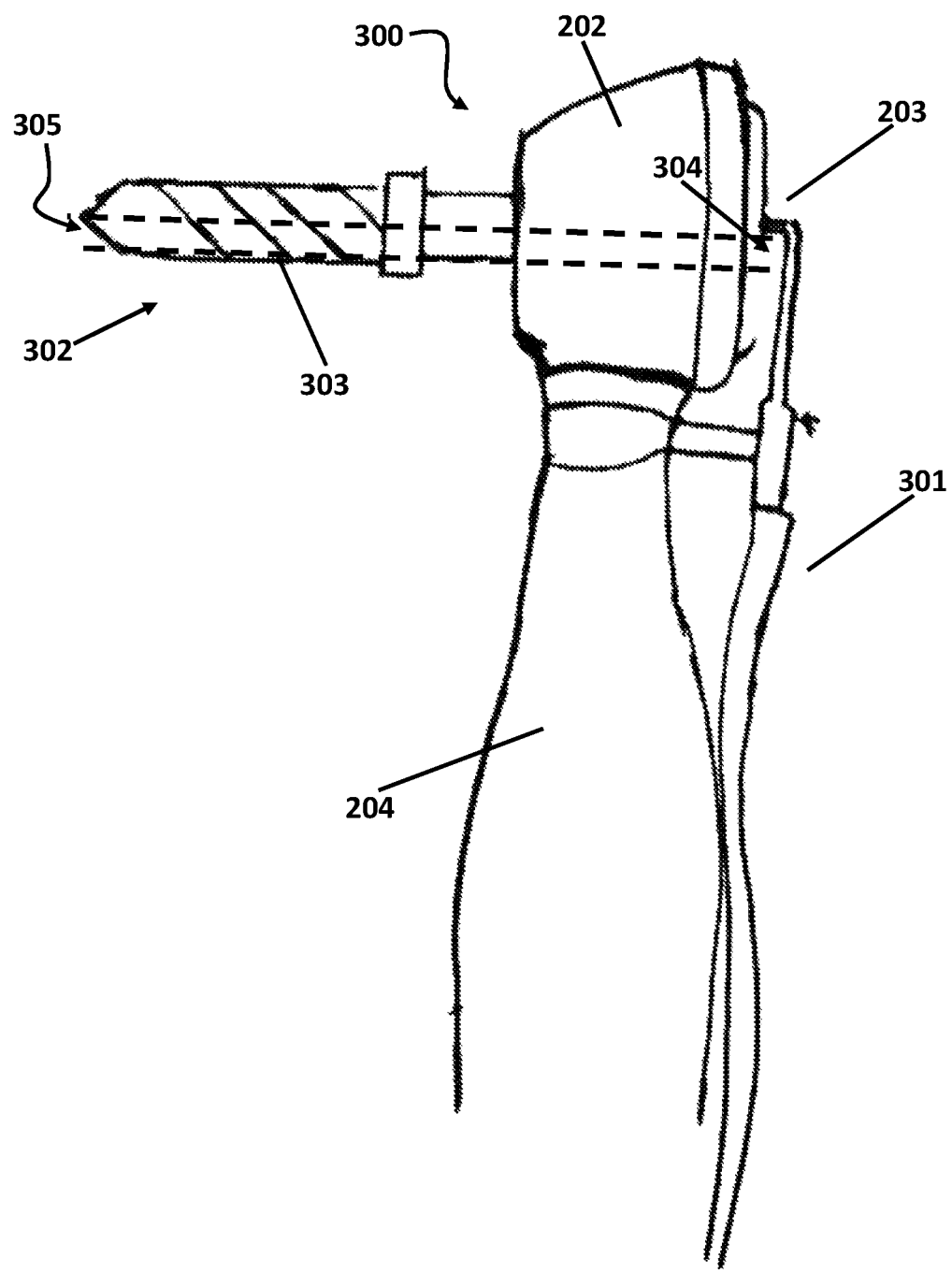
FIG. 3A shows a dental drill, according to exemplary implementations of the present disclosure.

FIG. 3A shows a dental drill 300, according to exemplary implementations of the present disclosure. As shown in FIG. 3A, the dental drill 300, may include a tube 301, a hollow drill burr 302, a head 202, an end cap 203, and a body 204.

Referring to FIG. 3A, the hollow drill burr 302 may have a central channel 303. The central channel 303 may have an inlet 304 and an outlet 305, the outlet 305 being at a distal end (visible but not separately numbered) of the hollow drill bur 302. The inlet 304 may be connected to tube 301 and the outlet 305 may be at the tip of the hollow drill burr 302.

The tube 301 may be configured to fluidically connect the hollow drill burr 302 to a liquid pressure regulator (not shown in the figure), to provide a constant liquid jet flow in the hollow drill burr 302. The tube 301 may be placed on the dental drill body 204.

Figure 3B:
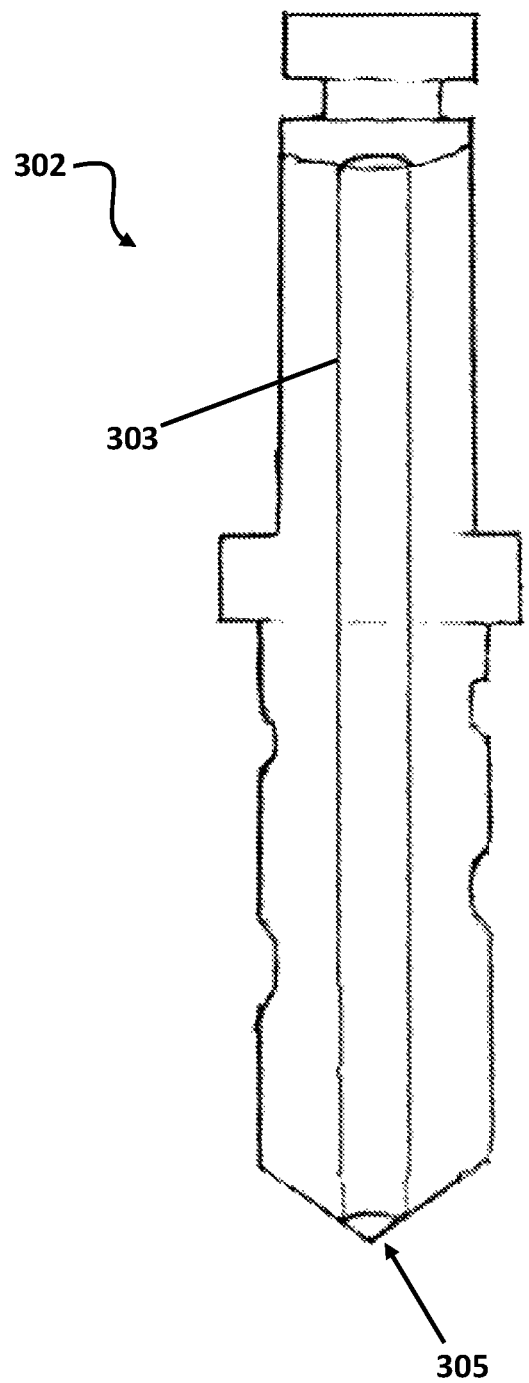
FIG. 3B shows a drill burr with a single channel, according to an exemplary implementation of the present disclosure.
Figure 3C:
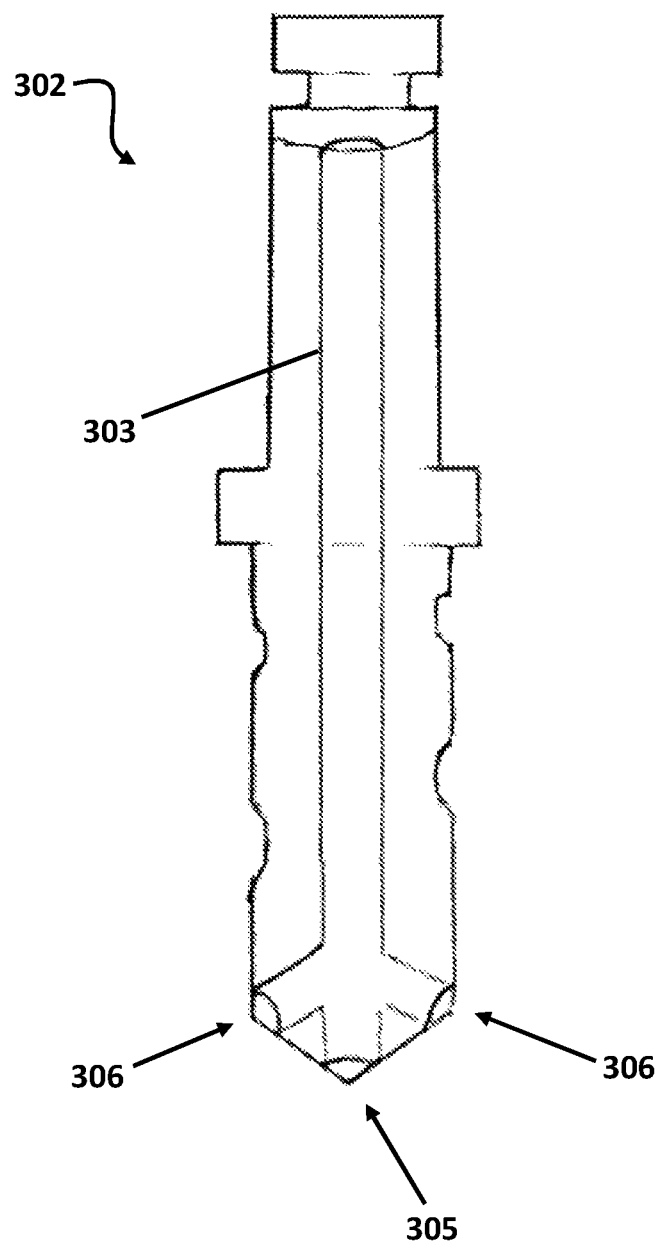
FIG. 3C shows a drill burr with side channels, according to an exemplary implementation of the present disclosure.

FIGS. 3B and 3C show hollow drill burrs 302, according to one or more exemplary implementations of the present disclosure. Referring to FIGS. 3B and 3C, the hollow drill burr 302 may be a drill burr with the central channel 303 made therein along the longitudinal axis of the hollow drill burr 302. The central channel 303 may be configured to supply the liquid jet flow on the drilling surface at the distal end, i.e., tip of the hollow drill burr 302.

Referring to FIG. 3C, in an implementation of the present disclosure, a plurality of lateral outlets or side channels 306 may be provided at the distal end of the hollow drill burr 302, branching from the central channel 303 and exiting near the outlet 305. The lateral outlets or side channels 306 may be configured to serve as paths for the liquid jet flow in case the outlet 305 is blocked or clogged.

Figure 4:
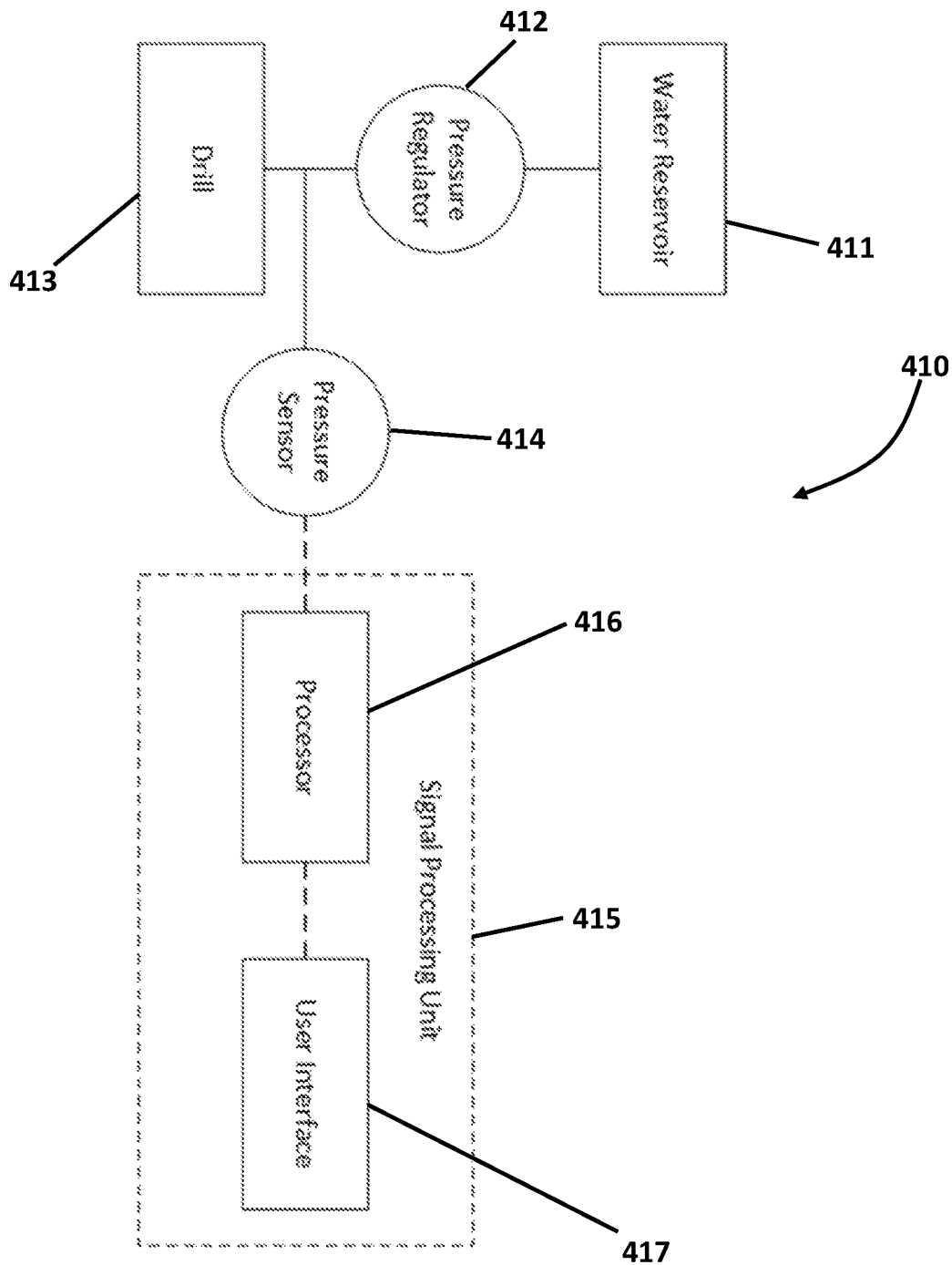
FIG. 4 illustrates a block diagram of a system for determining an internal structure of a bone along a drilling path, according to one or more aspects of the present disclosure.

FIG. 4 illustrates a block diagram of a system 410 for determining the internal structure of a bone along a drilling path, according to one or more aspects of the present disclosure, Referring to FIG. 4, the system 410 may include a water reservoir 411, a pressure regulator 412, a drill 413, a pressure sensor 414 and a signal processing unit 415.

The water reservoir 411 may be configured to provide a water flow in the system 410. The water reservoir 411 may be, for example, a water tank or urban water supply system. According to one or more exemplary implementations of the present disclosure, a pressure regulator 412 may be utilized to produce a constant-flow water flow. In other implementations of the present disclosure the pressure regulator 412 may be replaced with a constant-flow pump.

The water flow may be transmitted to the drill 413 via the pressure regulator 412 or a constant-flow pump. The pressure sensor 414 may be configured for measuring the liquid pressure in the line connecting the pressure regulator 412 to the drill, thereby measuring the pressure of the liquid jet that is ejected from the tip of the drill 413. The output signal of the pressure sensor 414 may be transmitted to signal processing unit 415.

According to some implementations, the signal processing unit 415 may include a processor 416 and a user interface 417. The processor 416 can include a generic digital signal processor (not separately visible) coupled by a bus to a memory configured to store computer executable instructions that, when execrated, cause the generic digital signal processor to perform methods and processes within methods according to this disclosure. The signals received from the sensor 414 may first be processed in the processor 416, to transform the signals received into meaningful, e.g., user-presentable information relating to the internal structural changes along the drilling path. The meaningful, user-presentable information may include, for example, an alert that may be conveyed to the surgeon via the user interface 417. The user interface 417 may be an LCD display, a buzzer, an alerting light, etc., by which the surgeon may be informed whether to continue the drilling or not.

According to one or more exemplary implementations of the present disclosure, the signal processing unit 415, may further include a signal amplifier (not shown in FIG. 4) that may be configured to amplify the signals received from the pressure sensor 414 before transmitting them to the processor 416.

Figure 5:
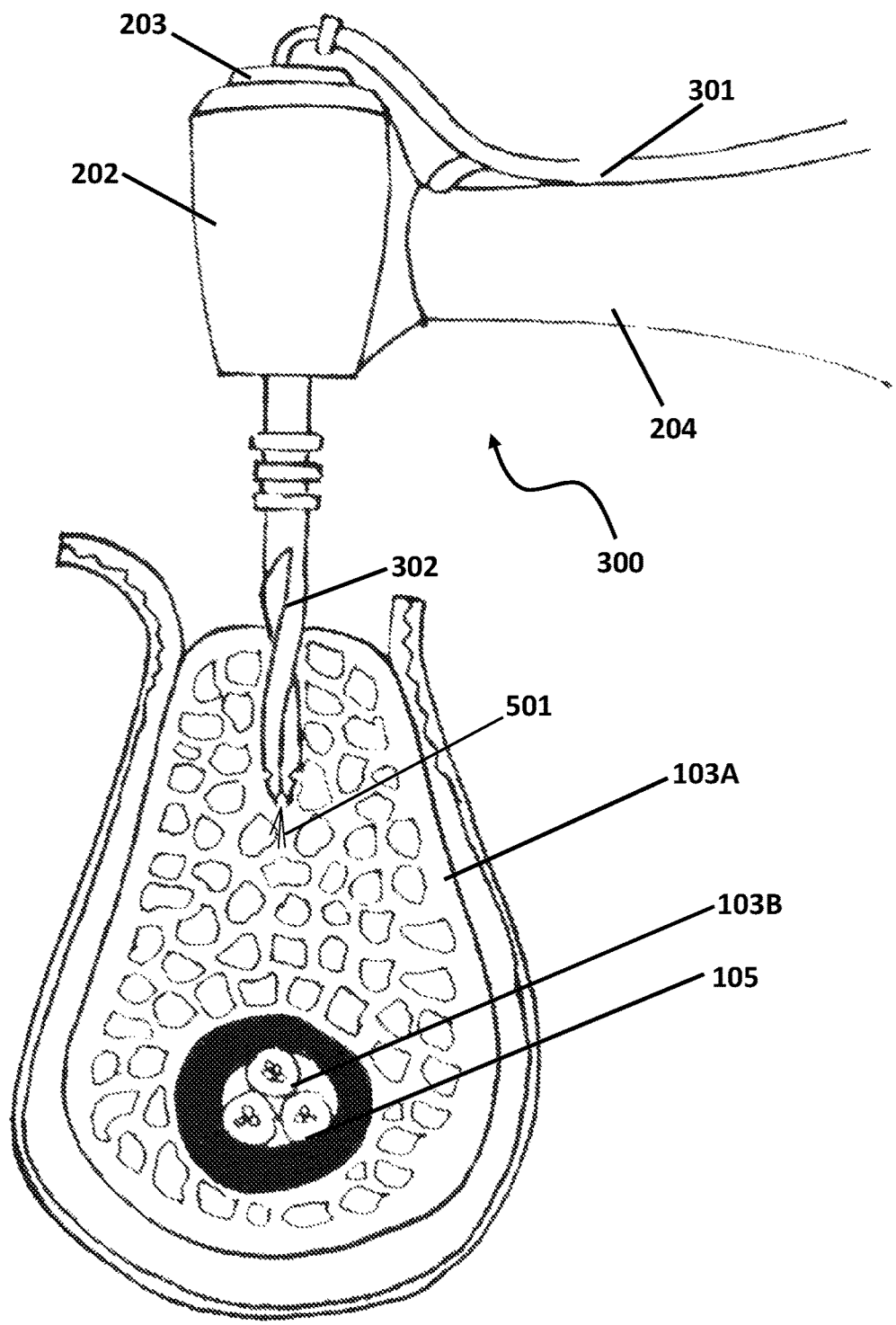
FIG. 5 shows a dental drill drilling into a mandibular bone, according to exemplary implementations of the present disclosure.

FIG. 5 shows the dental drill 300 while drilling through a mandible, according to exemplary implementations of the present disclosure. Referring to FIG. 5 the water flow may be provided from the water reservoir via a pressure regulator and it may be supplied to the drill 300 via the tube 301 and it may exit the tip of the drill burr as a liquid jet 501. The pressure of water in tube 301 that, corresponds to the pressure of the liquid jet 501 may be measured by the pressure sensor. When the hollow drill burr 302 passes from a first internal structure, such as cancellous bone 104 with a first material resistance to a second internal structure, such as or cortical bones 103A-B with a second material resistance, the pressure measured by the pressure sensor may change. This change in the pressure of water flow is due to a change in the internal structure of the bone through which the drilling is taking place. For example, cancellous bone 104 has a lower material resistance in comparison with cortical bones 103A-B, Therefore, the pressure of the liquid jet increases when the drill burr passes the cancellous bone 104 and reaches the cortical bone 103B. Referring to FIG. 4, this increase in the pressure may be sensed by the pressure sensor 414 and it may be transmitted as a signal to the signal processing unit 415 and then the processor 416 may cause the user interface 417 to send an alarm signal, such as a sound alarm, a light alarm or simply a graphical message on a display screen to inform the surgeon that the drill burr is now close to the cortical bone 103B near neurovascular bundle 105, i.e. the place that the surgeon wants to avoid drilling into.

EXAMPLE

Referring to FIG. 3A, in an exemplary implementation, the hollow drill burr 302 may be a 3 mm diameter cylindrical stainless steel burr with a 0.8 mm longitudinal central channel 303 made therein. The water jet provided at the tip of the hollow drill burr 302 via the line 301 has a base pressure of about 350 mmHg. As used herein, the base pressure is the pressure of the water jet before the drill bur is inserted inside a bone along the drilling path, i.e., there is no resistance in front of the water jet.

Referring to FIG. 5, in order to study the effect of a structural change along the drilling path on the pressure of the liquid jet 501, seven materials with different internal structures and material resistances were selected and then drilling was carried out inside these materials using the system of the present disclosure. The materials selected for this experiment were Plaster of Paris, dental stone, alginate, Polymethyl methacrylate (PMMA), cork, hard wood, and high porosity wood. Thirty holes were drilled in each sample. The base water pressure for each sample before drilling was recorded.

Referring to FIG. 4 a base pressure of the liquid jet is set to 350 mmHg by the pressure regulator 412 and then drill 413 was utilized for drilling into the seven material samples. The pressure of the liquid jet during the drilling process was measure by the pressure sensor 414 for each sample. The drilling test was replicated 30 times for each sample. The pressure of the liquid jet measured by the pressure sensor 414 was then sent to the signal processing unit 415. Mean pressure difference in the pressure of the liquid jet 501 was calculated for each sample that shows the effect of different structures and materials on the pressure of the liquid jet 501. Table 1 reports the mean pressure differences for these samples in mmHg. The measured pressure differences for different materials may be utilized in the signal processing unit 415 for converting the changes in the pressure of the liquid jet to meaningful information related to the structural changes in the bone along the drilling path.

TABLE 1

Mean pressure changes in different materials.

| | Plaster of Paris | Dental stone | Alginate | High porosity wood | Hard wood | Cork | PMMA |
|---|---|---|---|---|---|---|---|
| Number of Data | 30 | 30 | 30 | 30 | 30 | 30 | 30 |
| Mean Pressure Difference | 15 | 20.2 | 8.4 | 4.7 | 19.9 | 2.9 | 23.3 |

What is claimed is:

1. A system for determining an internal structure of a bone along a drilling path, the system comprising:
a drill;
a hollow drill burr, supported by and rotatable by the drill, extending along a longitudinal axis from a first end to a distal end, and including a central channel along the longitudinal axis, the central channel including an outlet at the distal end, wherein the distal end of the hollow drill burr extends distally outward from a substantially elongated body portion of the hollow drill burr, the hollow drill burr further including a plurality of side channels, the plurality of side channels including a first side channel, the first side channel branching from the central channel and exiting the hollow drill burr along a region corresponding to an intersection between the body portion and the distal end, the drill being configured to receive a liquid from a liquid reservoir, at a first pressure, and pass the liquid through the central channel while rotating the hollow drill burr, and the hollow drill burr being configured to direct the liquid, while drilling a bone, as a liquid jet directed at the bone;
a pressure sensor configured to sense decreases and increases in pressure in the liquid jet as the pressure changes from the first pressure to a second pressure; and
a signal processing unit configured to process said pressure change into information related to the structural changes in the bone along the drilling path from a first structure to a second structure.

2. The system of claim 1, wherein the liquid reservoir is configured to provide the liquid as a constant-flow liquid.

3. The system of claim 1, wherein the signal processing unit is configured to interpret said pressure change into information related to the structural changes based on corresponding the first structure to the first pressure and corresponding the second structure to the second pressure.

4. The system of claim 1, wherein the signal processing unit is further configured to send to a user-interface a user-detectable indicator in association with the information related to the structural changes.

5. The system of claim 4, wherein the user-detectable indicator is an audio alarm signal, and the user interface is configured to generate, in response, an audio alarm.

6. The system of claim 1, wherein the hollow drill burr is a dental drill burr.

7. The system of claim 1, wherein the distal end decreases in width as it approaches an outermost tip, and wherein the outlet of the central channel corresponds to an opening in the outermost tip.

8. The system of claim 7, wherein the distal end of the hollow drill burr is substantially conical in shape.

9. The system of claim 7, wherein: the hollow drill burr further includes an inlet at the first end, and the central channel extends between the inlet and the outlet.

10. The system of claim 1, wherein the first side channel branching from the central channel and at least partially exiting the hollow drill burr along an outermost surface of the body portion.

11. The system of claim 1, wherein the liquid includes water.

12. The system of claim 1, wherein the first side channel branching from the central channel and exiting the hollow drill burr along a first portion of the hollow drill burr, the outlet being further from the first end than the first portion of the hollow drill burr, the side channels being configured to serve as paths for the liquid jet flow in case the outlet is clogged.

13. The system of claim 1, wherein the first pressure is a pressure of the liquid before the hollow drill burr is inserted into the bone.

14. A method for determining an internal structure of a bone along a drilling path, the method comprising:

drilling a bone with a hollow drill burr having a distal end and a channel including an outlet at the distal end, wherein the distal end of the hollow drill burr extends distally outward from a substantially elongated body portion of the hollow drill burr, and a plurality of side channels branch from the channel, the plurality of side channels exiting the hollow drill burr along a region corresponding to an intersection between the body portion and the distal end;

while drilling the bone, receiving at the hollow drill burr a liquid at a first pressure, and passing the liquid through the channel to exit from the outlet as a liquid jet directed at the bone;

sensing a pressure in the liquid jet with a pressure sensor;

detecting, based on the sensing, an increase and decrease in a pressure in the liquid jet from the first pressure to a second pressure; and upon detecting the pressure change, generating a user-detectable information indicative of the pressure change.

15. The method of claim 14, wherein the liquid includes water.

16. The method of claim 14, further comprising transmitting an output signal of the pressure sensor to a signal processing unit.

17. The method of claim 16, further comprising amplifying the output signal of the pressure sensor by use of an amplifier before transmitting the output signal to the signal processing unit.

18. The method of claim 14, further comprising setting the first pressure to about 350 mmHg by use of a pressure regulator.

19. The method of claim 14, wherein a pressure of the liquid jet increases from the first pressure to the second pressure when the hollow drill burr passes from a first bone type with a first material resistance into a second bone type with a second material resistance that is greater than the first material resistance.

* * * * *